(12) United States Patent
Delgado

(10) Patent No.: US 11,071,477 B2
(45) Date of Patent: *Jul. 27, 2021

(54) HIGH FREQUENCY QRS IN BIOMETRIC IDENTIFICATION

(71) Applicant: Parallax Biometrics LLC, Houston, TX (US)

(72) Inventor: Reynolds Delgado, Houston, TX (US)

(73) Assignee: Parallax Biometrics LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,876

(22) Filed: Feb. 14, 2020

(65) Prior Publication Data

US 2020/0214597 A1    Jul. 9, 2020

Related U.S. Application Data

(63) Continuation of application No. 16/586,032, filed on Sep. 27, 2019.
(Continued)

(51) Int. Cl.
*A61B 5/117*    (2016.01)
*G06N 20/00*    (2019.01)
(Continued)

(52) U.S. Cl.
CPC .............. *A61B 5/117* (2013.01); *A61B 5/349* (2021.01); *A61B 5/7257* (2013.01);
(Continued)

(58) Field of Classification Search
CPC ..... A61B 5/7267; A61B 5/349; A61B 5/7257; A61B 5/117; A61B 5/30; G06N 20/00; G06N 3/082; G06N 3/08; G06N 3/0445; G06N 20/20; G06N 20/10; G06N 3/0454; G06N 5/003; G06N 7/005; G16H 50/70
See application file for complete search history.

(56) References Cited

U.S. PATENT DOCUMENTS 7,539,535 B1    5/2009    Schlegel et al.
8,924,736 B1    12/2014   Dusan
(Continued)

FOREIGN PATENT DOCUMENTS

GB    2570749 A  *  8/2019    ............... G06K 9/00

OTHER PUBLICATIONS

Adam Page et al., "Utilizing deep neural nets for an embedded ECG-based biometric authentication system", 2015, 2015 IEEE Biomedical Circuits and Systems Conference (BioCAS), pp. 1-4. (Year: 2015).*

*Primary Examiner* — Brenda C Bernardi
(74) *Attorney, Agent, or Firm* — Eric P. Mirabel

(57) ABSTRACT

Disclosed is sampling HF-QRS signals from a number of subjects (or derived values or features), and using e.g. deep learning-convolutional neural networks to find features or values which are (i) sufficiently similar for the same subject over all samples, yet (ii) sufficiently different among different subjects to allow identification. Also disclosed is finding signatures which are sufficiently stable over a particular period such that these signatures are within a deviation threshold, and then monitoring all subjects to be identified at least as often as the period used to establish the deviation threshold.

16 Claims, 6 Drawing Sheets

Related U.S. Application Data

(60) Provisional application No. 62/739,741, filed on Oct. 1, 2018.

(51) Int. Cl.
*A61B 5/00* (2006.01)
*G06N 3/08* (2006.01)
*A61B 5/349* (2021.01)

(52) U.S. Cl.
CPC ............ *A61B 5/7267* (2013.01); *G06N 3/08* (2013.01); *G06N 20/00* (2019.01)

(56) References Cited

U.S. PATENT DOCUMENTS

| | | | |
|---|---|---|---|
| 9,833,158 B2 | 12/2017 | Albert | |
| 2013/0173926 A1* | 7/2013 | Morese | G06F 21/32 713/186 |
| 2014/0088450 A1* | 3/2014 | Mottaiyan | A61B 5/316 600/521 |
| 2019/0147277 A1* | 5/2019 | Trigueiros Da Silva Cunha | G06N 20/10 382/115 |
| 2019/0150794 A1* | 5/2019 | Vrudhula | G06N 3/0454 |
| 2019/0236252 A1* | 8/2019 | Maeda | G06F 21/32 |
| 2019/0354660 A1* | 11/2019 | Fong | G06K 9/6262 |

* cited by examiner

Finding Signatures in HF-QRS Signals or Derived Features or Values

Using HF-QRS in Identification

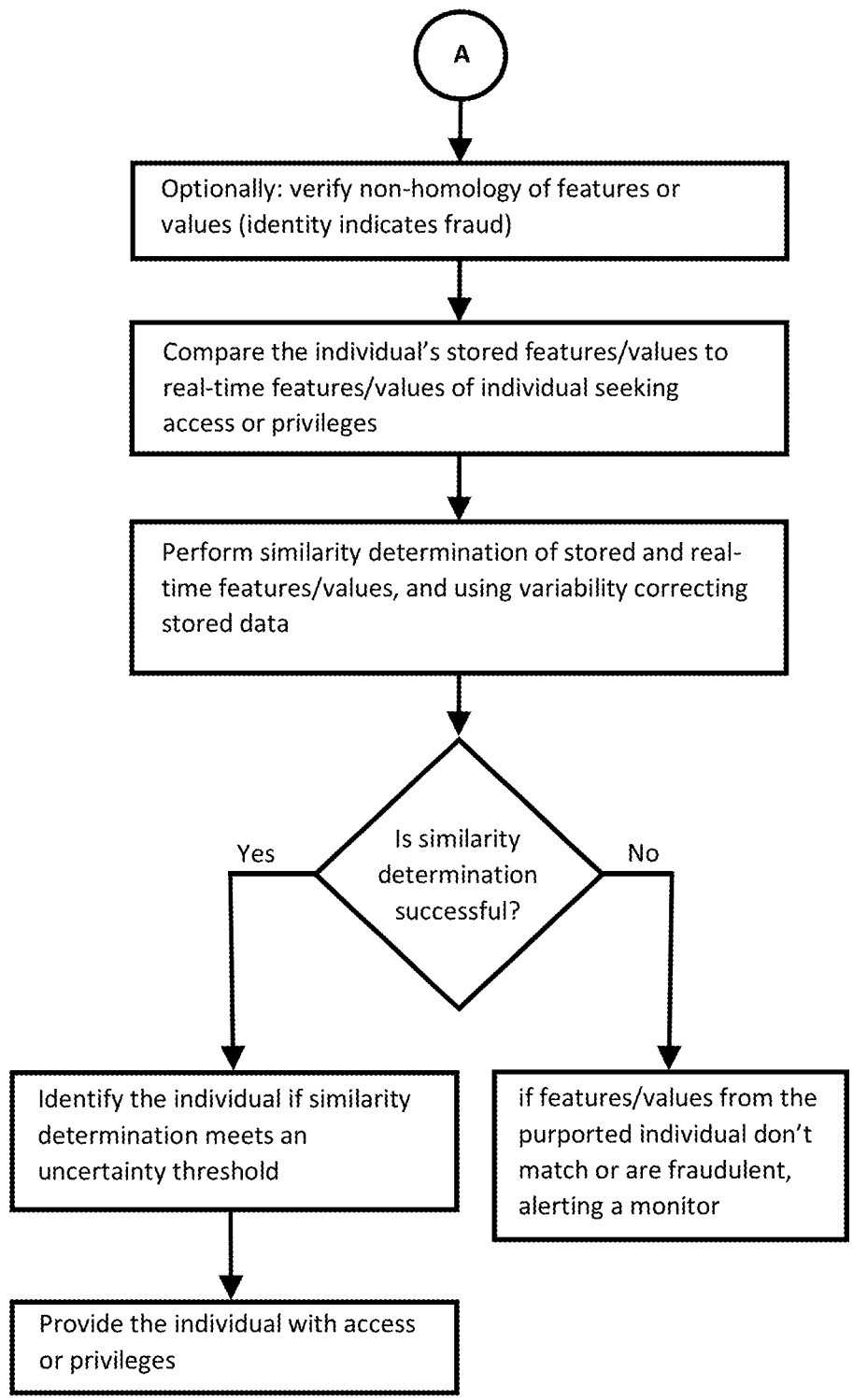

Verifying Stability of Biometric Signatures

STEP 1 - Test Phase: Choosing Identifiers and Deviation Threshold

Verifying Stability of Biometric Signatures

STEP 2 - Using Selected Identifiers; Monitoring Subjects

A) High resolution ECG

*Alignment and averaging*

B) Averaged ECG  2 mV

*Filtering (140 to 250 Hz)*

C) HFQRS signal  10 μV

⊢— 90 ms —⊣

D) Reduced Amplitude Zone (RAZ)

HFQRS envelope

*Quantification of RAZ in each lead*

E) 12 lead based index of ischemia

HIGH FREQUENCY QRS IN BIOMETRIC IDENTIFICATION

BACKGROUND

Most biometrics used today which rely on individual characteristics, including voice recognition, fingerprint, retinal and facial recognition, and are based on recognizable visible or audible characteristics, may be vulnerable to falsification, because technology allowing accurate copying and modification of such characteristics, i.e., CCD cameras, 3D printers and digital recordings, is widely used and available. Instruments for copying or modifying modified electrical signals, however, are not widely available. Generating an electrocardiograph (or ECG) requires a living and physically present individual at the identification site, making it more difficult to falsify. In addition, an ECG signal has all the properties of a secure biometric: universality, measurability, uniqueness, and permanence.

ECG signals can be transmitted for recording using conventional surface electrodes, usually mounted on the subject's chest. ECG signals are made up of several components representative of different functional stages during each heart beat, and projected according to the electric orientation of the generating tissues. There is a wide variety of subject-specific detail in electro-cardiologic signals due to variations in the heart tissue structure and orientation among individuals.

The ECG has been studied extensively as a potential biometric, but the inconvenience of the 12-lead detection, which was required, and insufficient reliability have inhibited widespread adoption. While it may be possible to use fewer leads, and to find unique portions of an ECG signal or a derived ECG signal, it has been difficult to find a reliable identifier using ECG signals where the subject's pulse rate varies (which it does on a continuous basis).

This electrical signal includes a sequence of PQRST complexes, and most PQRST sequences are not uniform. The time interval between two consecutive R signal peaks, referred to as an R-R interval, corresponds to a heart pulse, with a rate that normally lies in a range of 60-90 beats per minute (bpm). The P signal corresponds to atrial depolarization (right side, depolarizing first, followed by left side). The larger QRS complex corresponds to depolarization of the ventricles and repolarization of the atria. The T signal corresponds to repolarization of the ventricles. A weaker U signal occasionally appears.

A "wave" comprises a curve covering at least one complete component (P, Q, R, S and/or T). A time increment with a straight line amplitude extending between two consecutive signals, for example, from the end of an S wave to the beginning of an immediately following T wave, is referred to as a "segment." A time increment that includes at least one wave, with a graph that is at least partly curved, for example, from the beginning of a Q wave to the end of an S wave, is referred to as an "interval."

The QRS time interval, normally of temporal length 50-100 milli seconds (msec), represents conduction time from initiation of ventricular depolarization until the end of ventricular depolarization, and includes spread of the electrical impulse through the ventricular muscle. The P wave signal is normally gently rounded, and has a temporal length≈50-110 msec. A QRS interval greater than about 120 msec often indicates ventricular arrhythmia or a block of one of the bundles.

When the ECG was first developed for clinical use, a low-pass filter was implemented to eliminate the high-frequency "noise" in the signal to make it easier to assess the shape of the various waves and the length of the intervals in the displayed output. The high-frequency component of the QRS complex (HF-QRS) in the ECG signal—which is a distinct part of the ECG signal and is not the same as the ECG signal itself—was largely forgotten until researchers at NASA demonstrated it could be used to more precisely determine the health of the heart tissue, especially in relation to the electrical conducting system, as it more precisely represents the unique electrical conducting system of each person's heart. See U.S. Pat. Nos. 8,924,736; 7,539,535, both incorporated by reference. The volume of data present in the HF-QRS signal is significantly more than is present in standard low-frequency ECGs used today, and several patterns that NASA identified in the data have been shown to be relatively stable from month to month (T. T. Schlegel, et al. "Real-time 12-lead high-frequency QRS electrocardiography for enhanced detection of myocardial ischemia and coronary artery disease" Mayo Clin Proc, March 2004, Vol 79, pp. 339-50).

The number of features in the HF-QRS signal, and the amount of data that can be extracted from it, is considerably greater than other biometric identification measures currently monitor, for example, as compared with fingerprints, faces, conventional ECG readings, or retinal blood vessel patterns. Using the HF-QRS signal as a biometric therefore can permit making more reliable identification.

SUMMARY

Advancements in signal acquisition allow generation of a standard ECG signal from one or more sensors, preferably, electrodes (U.S. Pat. No. 9,833,158, incorporated by reference) including where the sensors are embedded in a smart-phone or other device (US Publ'n No. 2018/0116538; U.S. Pat. No. 8,615,290, both incorporated by reference). The sensor(s) can be on the surface of the smart-phone or device to establish connection using only minimal contact with a user, e.g., electrodes contacting the user through the fingertips instead of with adhesive connected or electrodes requiring skin-penetration. Sensors could also be remote and not in contact with the user—provided they can be electrically connected with the subject. Signals can also be collected and stored by cardiac-related implantable devices, such as pacemakers, A-fib monitors or defibrillators; or from any carried or wearable device, e.g., watches, smart-phones or eyeglasses. See U.S. Pat. No. 8,019,321 (incorporated by reference). They could also be embedded in a pacemaker, A-fib monitor or defibrillator.

Added optional security measures include verifying that a real-time HF-QRS signal (or derived data) from an individual is non-identical to the individuals stored biometric signature, as identity or close homology would indicate copying of existing data, and network infiltration or other fraud. Other fraud detection can also be included, e.g., measuring bio-impedance plethysmography and/or body heat to verify that a human subject is providing the sample.

Deriving the HF-QRS signals can be by following well-known methods, including band pass filtering the ECG signal preferably in the range of about 80 to 300 Hz, and more preferably from about 150 Hz to 250 Hz, or even over broader ranges that allow measurement of the HF-QRS. This filtered signal may be further amplified and filtered again to optimize the signal-to-noise ratio, and may be digitized, and/or analyzed with unique digital signal processing algorithms (as described below) to retrieve the information necessary to identify the individual in question. The extremely dense HF-QRS signals can optionally be further defined and limited by function, including, determining the root mean square (RMS) voltages over designated periods, or deriving other functions, including HFQE (described further below) to quantify HF-QRS changes; or HFAV (described further below) to reduce sensitivity to small variations in signal voltage.

In the invention, one samples the HF-QRS signals from a number of subjects (in some embodiments, following derivation of one of the values above, like RMS voltage, HFQE or HFAV) a number of times, to derive features or values which are (i) sufficiently similar for the same subject over all samples, yet (ii) sufficiently different among different subjects to allow identification. These set(s) of features or values are found using, e.g. deep learning-convolutional neural networks and either HF-QRS signals or values functionally derived from them. Suitable features may be present in particular HF-QRS signals or regions thereof, or in particular values derived from the HF-QRS signals. In one case, the features or values meeting criteria (i) also meet criteria (ii) above; in other cases the features and values meeting criteria (i) and (ii) are different.

The search for such features or values can be performed by first establishing a training set of such features or values, using features or values from a group of subjects, with each subject's HF-QRS representation in the group sampled a number of times. The training set can then be compared with a validation set (and/or cross-validated) for identifying overfitting and for additional verification of suitable features or values. One then finds such features or values, and, assuming finding features or values were properly derived and thus sufficiently similar to meet criteria (i) but sufficiently different to meet criteria (ii), they establish a signature for an individual.

Each individual's biometric signature is stored in a database for use in later identification. For identification, the stored biometric signature is compared to the features or values of a real-time, on-site HF-QRS signal taken from the individual, in order to identify the individual or determine no match to anyone in the database, and optionally, an alert to others in either or both the match and the no-match case. Real-time signals can also be temporarily or momentarily stored for later use.

With recent advances in signal processing, big data analysis, and machine learning techniques, HF-QRS signals from multiple individuals can be analyzed to find features meeting criteria (i) and (ii), and used to generate unique biometric signatures. A preferred approach is to fuse two or more signals or signal derivatives, such as fusing a spectrogram and a raw signal. A variety of signal derivative functions are also useful in determining values with sufficient differences among individuals for a signature.

An additional step, after finding features meeting criteria (i) and (ii), and using those results to generate biometric signatures, is to validate the stability of the signatures over time. This can be done with a set of test subjects, whose potential signatures (selected as above) are monitored over time. For any change (instability) of such identifiers, one would quantify changes over time, and then determine a deviation threshold for a theoretical subject, where an identifier for an individual within the deviation threshold is accepted; and one outside is rejected. Ultimately, all individuals whose identifiers are in the database should also be periodically monitored and the stored identifiers should be updated if there are significant changes (placing their signatures outside the deviation threshold).

Each time the HF-QRS of the individual is determined and sent for confirmation, there may be variations in the resulting data. Preferably variability correcting data is generated at the time of the biometric signature for the individual, and this variability correcting data is used during verification. This variability correcting data may comprise ambiguity resolving data which is used to reduce the sensitivity of values or features obtained from the individual, and/or error correcting data which is used by an error detection and correction algorithm to correct errors in the features or values (see also US Pat. No. 7,882,363, incorporated by reference).

Biometric identification has application across industries, including healthcare, security, forensics, finance, and consumer products. Digital keys (using HF-QRS as described herein) could be used for any internet-related security application, or any other type of secured privilege or access.

The invention includes determining the features or values of the HF-QRS signals or their HF-QRS functions or signal derivatives, which separately or cumulatively, are (i) sufficiently similar for the same subject over all samples, yet (ii) sufficiently different among different subjects to allow identification; and (iii) are sufficiently stable over time. The invention further includes comparing an individual's HF-QRS signals or his/her HF-QRS functions or derived values to a separately sampled signal, function or derivative value from the individual; and identifying the individual or determining no match to anyone in the database, and optionally, signaling others or storing in a database either or both the match and the no-match case.

BRIEF DESCRIPTION OF THE DRAWINGS

FIG. 2B is the second portion of the flow chart of FIG. 2A.

DETAILED DESCRIPTION

Figure 1:
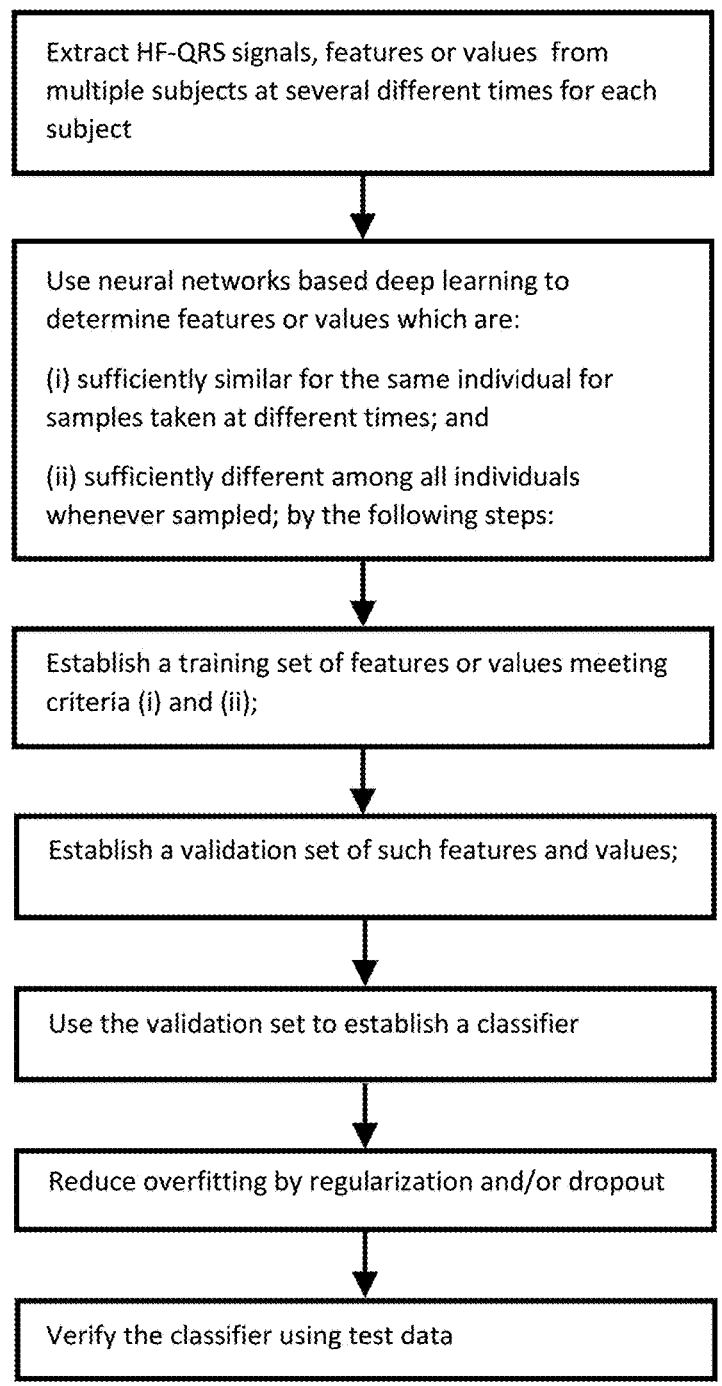
FIG. 1 is a flow chart showing how, using HF-QRS signals or derived features or values, biometric signatures for an individual are found through machine learning.

FIG. 1 is a flow chart showing how, with a neural network, to find biometric signatures in HF-QRS signals, or features or values derived from HF-QRS signals. The neural network allows one to find such signals, features or values which are: (i) sufficiently similar for the same individual for samples taken at different times; and (ii) sufficiently different among all individuals whenever sampled, to serve as biometric signatures. The method of finding datasets with such similarities and differences are well known, and can be accomplished using any of a variety of neural networks, which can perform deep learning. Similarly, establishing classifiers and using regularization to reduce overfitting is well known. The classifier can be a one-class SVM classifier or any of Naïve-Bayes; Logistic Regression, Support Vector Machine, Bayesian Network, Multilayer Perceptron, Deep Neural Networks, Random Forest or Adaboost.

Figure 2A:
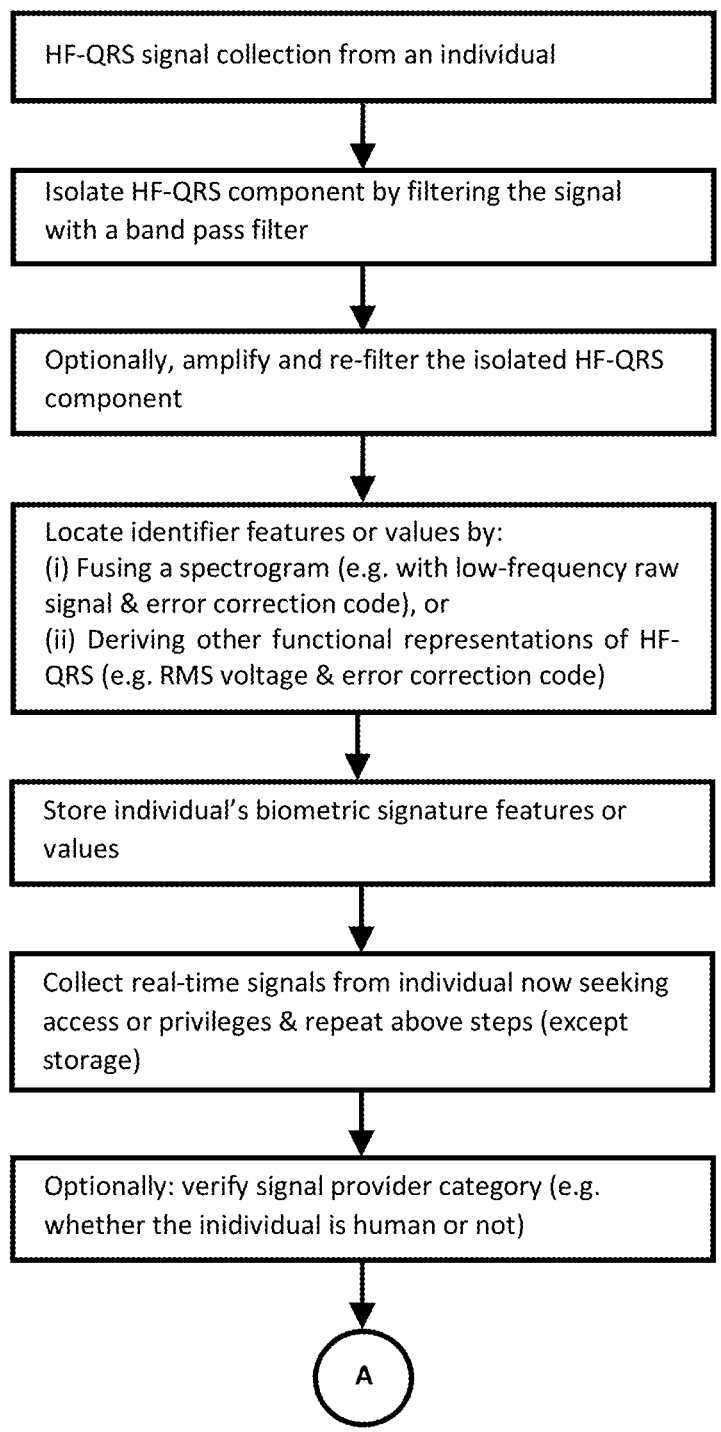
FIG. 2A is the first portion of a flow chart of utilizing a biometric signature of HF-QRS signals or derived features or values, for security-related applications, such as providing an individual entry or privileges.

FIGS. 2A and 2B are flow charts of deriving a HF-QRS signal and from it, deriving and storing an individual's biometric signature and then comparing it to a real-time signal for identification, and allowing some action by a properly identified individual; or alerting a monitor (a server or an individual) if there is an attempted security breach. The first step is to establish a dataset representing an individual's biometric signature using HF-QRS signals or derived features or values for the individual to be identified. The signals can be filtered, fused (as described below) or the features or values can be derived. At the time of identity verification, the individual's real-time signals, features or values are compared against the stored biometric signature, and if they pass a similarity threshold, the individual is identified and permitted access or privileges. Conversely, if there is no match, a monitor (a server or an individual) can be alerted.

Figure 3A:
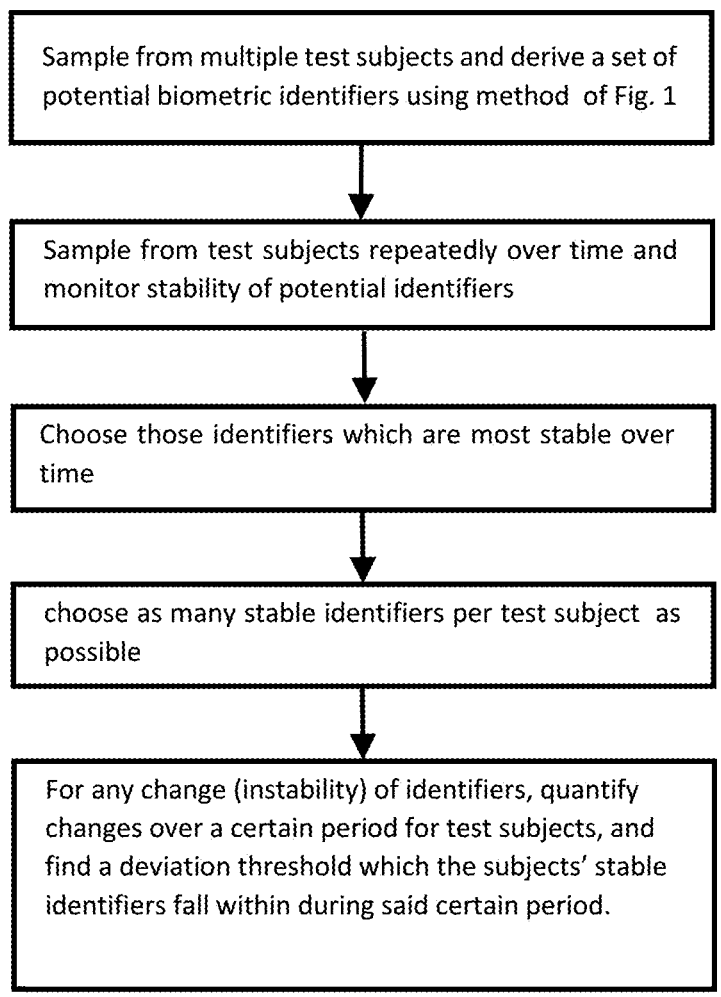
FIG. 3A outlines a test phase, in a flow chart, showing how to find and verify stability, over time, of biometric signatures selected in accordance with FIG. 1;' and, establishing a deviation threshold for the signatures.

FIG. 3A shows the first step, a test phase, in selecting signatures which are stable over time. A deviation threshold is also determined in the first step. The deviation threshold accepts signatures which have changed within its bounds, and rejects those that change beyond its bounds; thus anticipating some degree of change in signatures over time.

Figure 3B:
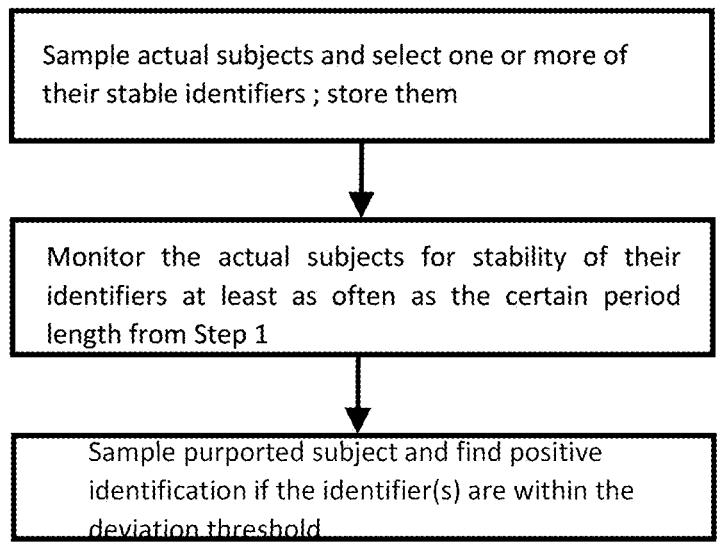
FIG. 3B outlines, in a flow chart, using a selected identifier in identification of a subject; and continued monitoring of subjects' signatures.

FIG. 3B shows the second step of using a selected signature, determined to be stable over time. If within the deviation threshold, the subject's signature is accepted, and the subject is granted access or privileges.

Methods for determining similar image features are described in U.S. Pat. No. 7,729,545 (incorporated by reference), and these methods can be applied to signals or fused signals, or other conventional similarity measures can be applied to derived functions or values.

As an optional step, the signals, features or values sent can be confirmed as of human origin using bio- impedance plethysmography (see U.S. Pat. No. 5,732,710, incorporated by reference) which measures electrical impedance in tissues, or a heat sensor. Bioimpedance can be measured by having the subject contact electrodes with different fingers (or other body part), then sending a weak electrical signal from one electrode and measuring the impedance at the other electrode, and to determine if the impedance corresponds with characteristic human impedance or not. A heat sensor could additionally or alternatively verify the subject had the body temperature characteristic of a human. The electrodes or sensors could be at a fixed location, like a door entry panel, or could be included on the individual's personal device, including in a cell phone.

As another optional step, the degree of homology between the stored and real-time features or values can indicate match, no match, or attempted fraud. The HF-QRS signals stored as biometric signatures are not expected to be identical to those obtained at another sampling.

Identity would indicate copying of an existing signal, feature or value set, and fraud. Homology thresholds can be established to differentiate match, no match and identity (fraud).

Another option is to examine the high frequency component of the P-R and S-T segments of an ECG, which, like HF-QRS, are data rich, and thus, variations are always expected at different samplings. Homology thresholds for these segments can also be established to differentiate match, no match and identity (fraud).

The verification data can be stored in the user device, in a local network or on the internet. Verified user data could act as a digital key for providing access, privileges or other security-related actions, whereas, identity could alert a monitor to fraud or attempted infiltration. A digital key can be provided on the user's device, such that the verified individual can use the digitally keyed device to provide access or privileges to any of a number of items.

Deriving Features and Values

Figure 4:
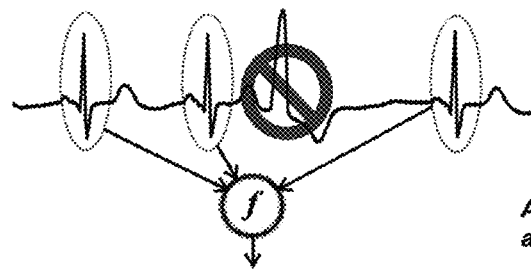
FIG. 4 depicts the steps of how one particular distinctive feature can be extracted from HF-QRS signals to be used as a biometric signature.
Figure 4:
Figure 4:
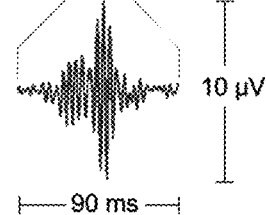
Figure 4:
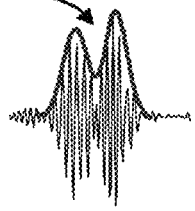
Figure 4:
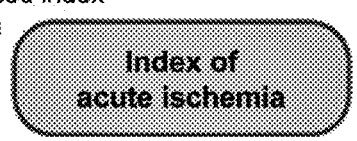

FIG. 4 depicts the steps showing how one particular such distinctive feature can be extracted from HF-QRS signals to be used as a biometric signature. In FIG. 4, step (a), one first determines an averaged or unaveraged ECG signal. ECG signals are determined in the 2 mV range. From that signal, one uses band pass filtering (most preferably, in the range of about 150 Hz to 250 Hz) to isolate an HF-QRS signal, in this case within a 10 μV range over a period of 90 milliseconds. From the derived HF-QRS signal, one can use the raw HF-QRS signal's contours as a biometric signature for an individual; or, one can isolate a reduced amplitude zone within the signal (see U.S. Pat. No. 7,539,535; US Publ'n No. 2018/0116538, both incorporated by reference, describing monitoring HF-QRS signals, and finding the reduced amplitude zones). Both the raw HF-QRS signal's contours and the reduced amplitude portion of the signal can be sufficiently distinctive among individuals, yet similar for the same individual over multiple samplings, to allow derivation of signatures from it; as described herein.

In finding distinctive features, it may be useful to augment the HF-QRS signal by changing the scale, or changing the attenuation or gain of particular waves. This can also be applied to the P-R and S-T segments of an ECG, if they are being monitored for added security, as noted above.

Another value which can be derived from an HF-QRS signal, and used for biometric signatures, is an RMS voltage value. It is derived from the filtered HF-QRS signal by the following steps (see Xue et al., p. 240, col. 2): The QRS onset and offset (fiducial points) of the averaged unfiltered waveforms (uqon, uqoff) are determined using the spatial velocity of the three leads and the unfiltered QRS duration is measured (UQRSD=uqoff–uqon). Data of each lead are preferably filtered (150-250 Hz) using a spectral filter. Vector magnitude (VM) of the three filtered signals (fX, fY, and fZ) was computed as $VM=(fX^2+fY^2+fZ^2)^{1/2}$. Average noise level (AVNL) can be measured in the ST-segment in a 40-ms window located 60 ms from the unfiltered QRS offset. Filtered QRS fiducial points (fqon and fqoff) can be determined in the VM waveform using a threshold equal to two times the measured AVNL and the filtered QRS duration is measured (FQRSD=fqon–fqoff). The RMSV can be computed for all of the samples in the VM waveform, VW, for the duration of the FQRSD, as $$RMSV = \sqrt{\frac{\sum_{i=fqon}^{fqoff}(VMi-AVNL)^2}{FQRSO}} \quad (1)$$

Xue et al. also determined a new value, HFQE, to quantify HF-QRS changes. RMSV is first computed using the unfiltered QRS fiducial points and the unfiltered QRS duration (uqon, uqoff, and UQRSD) instead of the filtered fiducial points and the filtered QRS duration as in equation 1. The HFQE is computed from the filtered signals using the unfiltered QRS fiducial points, plus a padding of samples corresponding to an additional duration of 10 ms before uqon and 10 ms after uqoff:

$$HFQE = \sum_{i=uqon-10\ ms}^{uqoff+10\ ms} (VMi - AVNL)^2 \quad (2)$$

Xue et al. also determined a third value, HFAV, to reduce sensitivity to small variations in signal voltage, using the function:

$$HFAV = \sum_{i=uqon-10\ ms}^{uqoff+10\ ms} |VMi - AVNL| \quad (3)$$

Xue et al. also noted that the unfiltered QRS duration was more stable than the filtered QRS duration, for all the groups they tested.

Any of RMSV, HFQE and HFAV, or other suitable derived features or values, can be used in the biometric identification described herein.

Aversano et al. describe data manipulation steps where the RMS voltage of the extremely dense HF-QRS signals can optionally be further defined and limited by: (i) Fourier transforming the data and attenuating the low frequency harmonics, followed by inverse Fourier transformation to obtain filtered signals, from which onset and offset of QRS is determined, followed by determination of the root mean square voltage for the entire QRS complex; (ii) as a further optional step, determining the local peaks and valleys of filtered waveforms, and finding the envelopes of the high frequency ECG by depicting a joining of the peaks and valleys; (iii) also optionally, determining the coefficient of variation and mean standard deviation from a group of subjects, in order to determine an appropriately high confidence limit (eg., 95%) for variability in HF-QRS root mean square (RMS) voltage, so that RMS voltage results outside that confidence limit can be discounted or ignored. Such RMS voltages can be used in the biometric identification described herein.

The initial signal for deriving the RMS voltage value can be any representation of the HF-QRS, including distinctive features which can be preferentially determined by deriving a spectrogram of the HF-QRS signal (I. Odinaka et al., "ECG Biometrics: a robust short-time frequency analysis," WIFS'2010, Dec. 12-15, 2010; J. da Silva Luz et al., "Learning Deep Off-the-Person Heart Biometrics Representations," IEEE TRANSACTIONS ON INFORMATION FORENSICS AND SECURITY, VOL. 13 pp. 1258-70 (2018)). A spectrogram is the visual representation of the energy of a signal expressed as a function of frequency and time. If one wishes to not derive RMS voltage values and related functions, but instead use the spectrogram itself, the spectrogram is preferably fused, in one example with the low frequency raw signal (see J. da Silva Luz et al. supra) so that a single heartbeat is represented with two separate views, which reduces the system error. Another option is to derive RMS voltage and related values (HFQE and HFAV) or other values or features, manually from the time-series, or spectrogram, or from both, or to provide an unsupervised derivation ("automatic" in a sense) for the time-series, spectrogram, or from both. Further, even the spectrogram itself or the raw signal itself can be analyzed further to extract distinctive features, instead of extracting them from the fused result.

Deriving and Using Features or Values

Features or values which allow discrimination of individuals can be extracted using an unsupervised deep learning algorithm or by manually identifying features. The spectrogram, low frequency raw signal, or the fused results (spectrogram with low frequency raw signal), or RMS voltage and related values (HFQE and HFAV) or other values or features can be used to find one or more classifiers by fitting to a training set with a deep learning algorithm. See V. Jindal et al., "An Adaptive Deep Learning Approach for PPG-Based Identification" IEEE pp. 6401-04 (2016). Or, such common features can be manually identified and extracted. A preferred deep learning algorithm is a convolutional neural network (CNN), which given a large amount of data, can learn deep (several layers) and discriminate representations and classifiers directly from the data itself. Other suitable deep learning algorithms include a deep neural network ("DNN"), long short-term memory recursive neural network ("LSTM-RNN"), or a Convolutional, Long Short-Term Memory Deep Neural Network ("CL-DNN").

The same features or values in the training set, i.e., one of: fused results (spectrogram with low frequency raw signal), or RMS voltage and related values (HFQE and HFAV) or other features or values, taken either or both at different times or from different subjects, are used as the validation sets and the test sets. The validation set is used to tune the hyperparameters of the classifier and avoid overfitting, e.g., by using the validation set for regularization. In one simple example, regularization is by early stopping of training, when the error on the validation dataset increases, as this is a sign of overfitting to the training dataset. Overfitting can also be reduced by using dropout, which regularizes the objective function by randomly setting a certain percentage of nodes in the neural network to zero (ignoring them) during training.

Other modifications to enhance results include data augmentation, to force the network to recognize the heartbeat even when some portions are compromised (by pulse or physiological changes in the subject). The modifications include replicating the heartbeat of a training dataset in other versions of the heartbeat, where the new versions are generated by changing the scale, or changing the attenuation or gain of particular waves, by a specified percentage. J. da Silva Luz et al., supra.

The signal features or values are then classified, as in Choi et al., "Biometric Authentication Using Noisy Electrocardiograms Acquired by Mobile Sensors" IEEE pp. 1266-73 (2016), by an appropriate one-class classifier, where a one-class Support Vector Machine (SVM) classifier is preferred, but can also include: Naive-Bayes; Logistic Regression, Support Vector Machine, Bayesian Network, Multilayer Perceptron, Deep Neural Networks, RBF Network, Bagging, Random Forest and Adaboost. Choi et al. designed a cascading bandpass filter for noise cancellation and suggested eight fiducial features. For classification-based authentication, they used the radial basis function kernel-based support vector machine, which showed the best performance among nine classifiers through experimental comparison. Upon classification, the chosen one-class machine learning algorithm will determine if the input function or values matches those in the database. Those that do not match may be measured again.

The embodiments, components, steps, features, objects, benefits, and advantages which have been discussed are merely illustrative, and not limiting. All articles, patents, patent applications, and other publications that have been cited in this disclosure are incorporated herein by reference.

Relational terms such as "first" and "second" and the like may be used solely to distinguish one entity or action from another, without necessarily requiring or implying any actual relationship or order between them. The terms "comprises," "comprising," "including" and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type. The invention is defined only in the claims which follow and includes all equivalents of the elements in the claims.

What is claimed is:

1. A method for identification/verification of an individual comprising:
   sampling HF-QRS signals or derived features or values from a group of subjects, with each sampling performed at several different times for each subject;
   using deep learning neural networks to determine features or values which are: (i) similar for the same individual for samples taken at different times; and (ii) different enough among all individuals whenever sampled, to function as biometric signatures;
   sampling said features or values from individuals and storing them in a database as each of their respective biometric signatures; and
   sampling, at a later time, said features or values from an unknown individual and determining if they match any of the stored biometric signatures features or values.

2. The method of claim 1 further including permitting access or privileges to the unknown individual if their biometric signature is a match to a stored biometric signature.

3. The method of claim 1 further including alerting a monitor if the unknown individual's biometric signature does not match to a stored biometric signature.

4. The method of claim 1 wherein the deep learning neural networks are one or more of a convolutional neural network, a deep neural network, long short-term memory recursive neural network, and a convolutional, long short-term memory deep neural network.

5. The method of claim 1 wherein the features or values which function as biometric signatures are determined by first establishing a training set of features or values from the group of subjects, with each subject's HF-QRS sampled a number of times; comparing the training set with a validation set for identifying overfitting of a classifier and for additional verification of suitable features or values.

6. The method of claim 5 wherein the classifier is a one-class SVM classifier.

7. The method of claim 6 wherein the classifier is one of: Naïve-Bayes; Logistic Regression, Support Vector Machine, Bayesian Network, Multilayer Perceptron, Deep Neural Networks, Random Forest and Adaboost.

8. The method of claim 5 further including comparing the training set with a validation set for verification of the features or values which function as biometric signatures.

9. The method of claim 5 further including reducing overfitting by regularization.

10. The method of claim 9 wherein the regularization uses dropout.

11. The method of claim 1 wherein the deep learning neural networks use band pass filtering for the HF-QRS signals and/or derive other functional representations of HF-QRS or regions thereof, including one or more of root mean square voltage, HFQE and HFAV, to determine said features or values.

12. The method of claim 11 further including further defining and limiting HF-QRS signals by: (i) Fourier transforming the data and attenuating the low frequency harmonics, followed by inverse Fourier transformation to obtain filtered signals, from which onset and offset of QRS is determined, followed by determination of the root mean square voltage for the entire QRS complex; and/or (ii) determining local peaks and valleys of filtered waveforms, and finding envelopes of a high frequency ECG by depicting a joining of the peaks and valleys; and/or (iii) determining the coefficient of variation and mean standard deviation in HF-QRS signals, features or values from a group of subjects, in order to determine variability therein.

13. The method of claim 12 wherein matching is determined if said features or values from the unknown individual against stored features or values meet a similarity threshold.

14. The method of claim 11 wherein band pass filtering is for frequencies from about 150 Hz to 250 Hz.

15. The method of claim 1 further including the steps of:
   monitoring selected biometric signatures of a group of test subjects over time to find stable signature(s), which are stable over time;
   determining a deviation threshold from the monitoring such that said test subjects' stable signatures fall within the deviation threshold over the period measured;
   determining whether the stable signatures derived from actual subjects fall within the deviation threshold.

16. The method of claim 15 further including sampling a signature from an unknown subject and determining that it matches one of the stored signatures if it is within the deviation threshold.

* * * * *